United States Patent [19]

Agdanowski et al.

[11] Patent Number: 4,598,707
[45] Date of Patent: Jul. 8, 1986

[54] MEDICAL TUBE WITH INFLATION CUFF

[75] Inventors: Ronald T. Agdanowski, St. Peters; James A. Geil, St. John, both of Mo.

[73] Assignee: Sherwood Medical Company, St. Louis, Mo.

[21] Appl. No.: 622,950

[22] Filed: Jun. 21, 1984

[51] Int. Cl.⁴ ............................................. A61M 25/00
[52] U.S. Cl. ................................. 128/207.15; 604/99; 604/100
[58] Field of Search .................................... 128/207.15; 604/96–103, 247, 256; 251/342

[56] References Cited

U.S. PATENT DOCUMENTS

| 274,447 | 3/1883 | Kennish | 604/247 X |
| 3,407,817 | 10/1968 | Galleher | 128/207.15 |
| 3,654,932 | 4/1972 | Newkirk et al. | 604/247 X |
| 3,707,146 | 12/1972 | Cook et al. | 128/2 R |
| 3,794,043 | 2/1974 | McGinnis | 128/349 BV |
| 3,818,903 | 4/1973 | Bleecker | 128/349 BV |
| 3,841,319 | 10/1974 | Michael et al. | 128/28 |
| 3,854,484 | 12/1974 | Jackson | 128/351 |
| 3,861,394 | 1/1975 | Villari | 604/129 |
| 3,901,246 | 8/1975 | Wallace | 128/207.15 |
| 4,022,217 | 5/1977 | Rowean | 128/207.15 |
| 4,102,342 | 7/1978 | Akiyama et al. | 604/99 X |
| 4,526,196 | 7/1985 | Pistillo | 128/207.15 X |

Primary Examiner—Dalton L. Truluck
Attorney, Agent, or Firm—Stanley N. Garber; Andrew J. Beck; William R. O'Meara

[57] ABSTRACT

A medical tube with an inflatable cuff is provided with a cuff inflation control unit that includes a pressure indicating balloon, a duck-bill valve extending into the balloon, and an elastomeric pump bulb connected to the valve and balloon for pressurizing the cuff.

19 Claims, 6 Drawing Figures

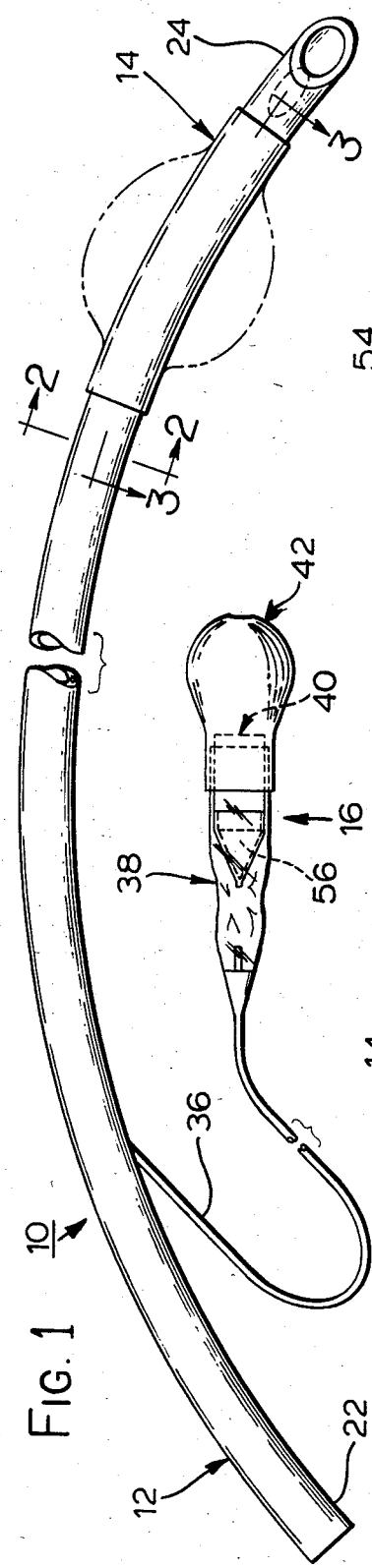
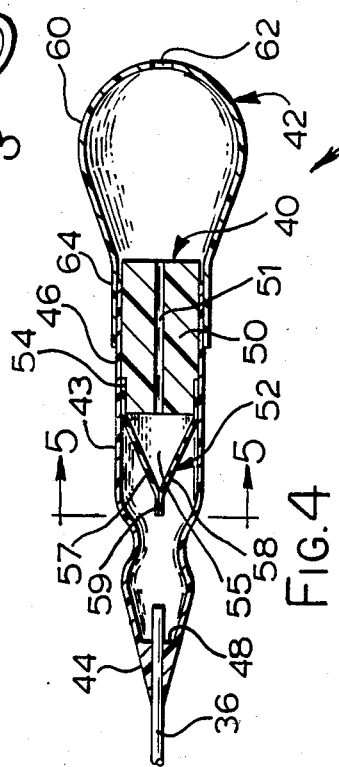
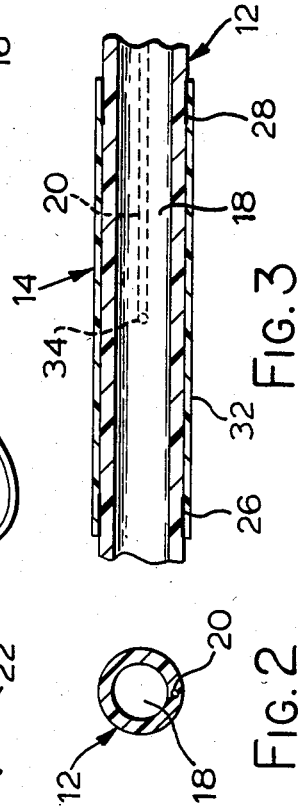
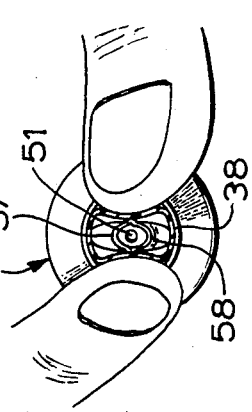
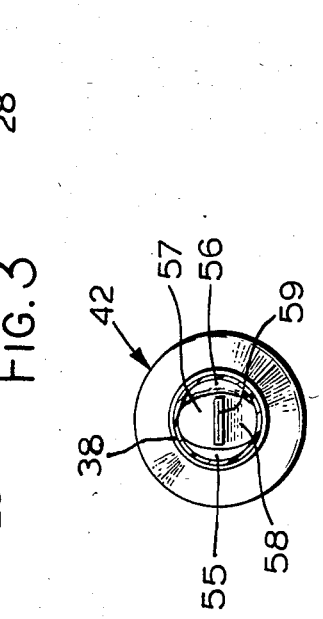
FIG. 1
FIG. 2
FIG. 3
FIG. 4
FIG. 5
FIG. 6

MEDICAL TUBE WITH INFLATION CUFF

TECHNICAL FIELD

This invention relates to medical tubes with inflatable cuffs and, more particularly, to an inflation control unit for the cuff of a medical tube.

BACKGROUND ART

Inflatable cuffs are provided on various types of catheters and medical tubes to close-off a body passageway between the tube and the sidewalls of the passageway. For example, endotracheal and tracheotomy tubes may be provided with cuffs to close off the trachea of a patient while supplying air or other gas to the lungs. It has been common practice to connect a valve in fluid communication with the cuff that is constructed to receive the tip of a syringe barrel. A piston slidable in the barrel forces air through the tip and valve to inflate the cuff within the passageway of the patient. Generally, when the barrel tip is inserted into the valve, the valve opens, and when the tip is removed, the valve closes to maintain the cuff inflated. A pilot or pressure indicating balloon is often connected to the cuff to provide a visual indication of the pressure condition within the cuff.

Such cuff inflation systems have certain disadvantages or problems associated with them. For example, when it is desired to inflate the cuff, a syringe must be located, unpackaged, and the barrel tip inserted into the valve, with such insertion generally requiring the use of both hands. The syringe must then be removed from the valve to allow the valve to close. Sometimes adjustment of the pressure within the cuff is required because of an increase or decrease in the cuff pressure as result of gas permeating the cuff or because of an air leak in the inflation system. Each time the pressure is adjusted, a syringe must be located and the tip again inserted into the valve to adjust the air pressure in the cuff, and then the syringe is again removed from the valve. Thus, use of the above type of syringe and valve is somewhat complicated and generally involves a considerable amount of time to use. Also, there is a chance of misplacing the syringe or of having difficulty in finding a syringe when needed.

In U.S. Pat. Nos. 3,707,146 and 3,841,319, hand pumps in the form of elastomeric bulbs are employed to inflate the tube cuffs. A pressure indicating balloon is also used in the latter patent. The cuff inflation systems of these patents do not require a separate syringe that must be connected and disconnected each time air is injected into or ejected from the cuff. However, such pumps generally include relatively complicated and expensive rotary valves.

Such rotary valves generally employ metal valve parts and a vent arrangement at the valve. Also, a one-way intake valve such as a ball valve, is generally required at the end of the pump bulb. Since medical tubes or catheters are generally of the "disposable" type, that is, intended for single-use or one patient only, and then discarded, hand pumps of this type would cause the cost of the medical to be exceedingly high.

DISCLOSURE OF THE INVENTION

It is therefore an object of the present invention to provide an improved medical tube and cuff inflation control unit which overcomes one or more of the above-mentioned problems.

Another object is to provide an economical medical tube with a cuff and a cuff inflation control having parts that are continuously connected together, economical, arranged in a highly efficient and compact construction, and wherein the medical tube lends itself to single-patient use.

In accordance with one aspect of the present invention, a medical tube is provided with an air inflatable cuff, a pressure indicating balloon in fluid communication with the cuff, and a duck-bill valve connected between the indicating balloon and a manually operated pump which is edapted to affect air flow in one direction through the valve for inflating the cuff. The duck-bill valve can be manually squeezed to open the valve and allow air to flow therethrough in the opposite direction for reducing pressure in the cuff.

These, as well as other objects and advantages of the present invention, will become more apparent from the following detailed description and accompanying drawing.

BRIEF DESCRIPTION OF THE DRAWING

FIG. 1 is a side view of a medical tube in accordance with a preferred embodiment of the present invention;

FIG. 2 is a cross-sectional view taken along 2—2 of FIG. 1;

FIG. 3 is a cross-sectional view on an enlarged scale, taken along line 3—3 of FIG. 1;

FIG. 4 is a longitudinal cross-sectional view, on an enlarged scale, of the inflation control unit of FIG. 1;

FIG. 5 is a cross-sectional view taken along line 5—5 of FIG. 4; and

FIG. 6 is a cross-sectional view similar to FIG. 5 but illustrating pressure being manually applied to the opposed ends of the duck-bill valve of FIG. 5 to open the valve.

DETAILED DESCRIPTION OF THE PREFERRED EMBODIMENT

Referring now to the drawing and particularly to FIG. 1, a medical tube device, shown in the form of an endotracheal tube, is indicated generally at 10. The endotracheal tube 10 is shown including a main airway tube or shaft 12, an expansible or inflatable cuff 14, and a cuff inflation control unit indicated at 16 for selectively controlling the inflation and deflation of cuff 14.

The tube 12, as shown also in FIGS. 2 and 3, has a main airway lumen 18 and a cuff inflation lumen 20 extending longitudinally within the sidewall of the tube. Tube 12 may be formed of a suitable material, such as rubber or plastic, for example, a thermoplastic material such as polyvinyl chloride or the like. The tube may be extruded and should be semi-rigid but capable of bending. Tube 12 is open at its proximal and distal ends, which are indicated at 22 and 24, respectively.

Cuff 14 is preferably of the elastic "tight-to-shaft" type as shown, that is, the cuff is formed, such as by extrusion, molding or dipping into a generally cylindrical shape, and such that when disposed on the tube, all or the major portion of the inner surface of the cuff is closely adjacent to and may be in contact with the outer surface of the tube 12 in its deflated condition. The cuff is preferably formed of an elastic material, such as natural or synthetic rubber, or a suitable elastomeric thermoplastic material. A latex or silicone rubber, for example, may be used. Cuff 14 is secured to tube 12 adjacent the distal end 24 of the tube, which end is adapted to be inserted into the trachea of a patient. Opposed end portions of cuff 14 are fixed in sealing relation to the outer surface of tube 12, such as by an adhesive, solvent bonding, heat bonding or in any other suitable manner. In FIG. 3, rings of adhesive material are indicated at 26 and 28 which seal the opposed ends of the cuff to the tube 12. The central inflatable or expansible portion of cuff 14, indicated at 32, is, of course, able to move away from tube 12 when the cuff is inflated, the cuff assuming a bulbous form as indicated in FIG. 1 by the phantom lines about the cuff. The inflation lumen 20 connects with a sidewall opening 34 (FIG. 3.) disposed between the opposed ends of the cuff and directly under the inflatable cuff portion 32. The inflation lumen 20 ends or is closed distally of the sidewall opening 34. Lumen 20 is thus in fluid communication with the interior of cuff 14. The proximal end of the inflation lumen 20 is connected in fluid-tight connection with one end of an inflation conduit or tube 36 that is secured, such as by an adhesive solvent, heat bonding or other suitable means, to the tube 12.

The cuff 14 may be preshaped if desired to have a bulbous form when inflated under slight inflation pressures. In such case, the cuff may be made of a plastic which is not elastic or mildly elastic, such as urethane, polyvinyl chloride or the like. Because the elastomeric "tight-to-shaft" cuff is capable of quickly and fully collapsing when deflated for easy removal of the medical tube from the patient, it is preferred to the type which is preformed in the bulbous form and which generally becomes irregular in shape when deflated. Either type of cuff can be used.

The cuff inflation control unit 16, as shown also in FIG. 4, includes a pilot or pressure indicating balloon 38 connected to the opposite end of inflation conduit 36, a valve member 40 connected to the proximal end of balloon 38, and a manually operated air pump in the form of a hand-operated, air pressure generating, resilient, elastomeric bulb 42 for effecting air pressurization and inflation of cuff 14 and balloon 38.

Balloon 38 may also be of the "tight-to-shaft" type but is shown of the preformed or molded type so that it normally has a generally bulbous central portion 43 that is expansible or inflatable, and in the uninflated condition may be irregular in shape as shown. The balloon has a left or distal end portion 44 and a proximal sleeve portion 46. Sleeve 46, which is part of the balloon, is preferably integrally connected with the bulbous portion 43 although it may be a separate part connected to bulbous portion 43 of the balloon. The distal portion 44 of the balloon is sealingly connected to the proximal end of the inflation conduit 36 by an integral support member 48 which may be a melt-molded portion of the balloon 38. The support member 48 may be a separate member of a suitable plastic which is sealed to the outer surface of conduit 36 and the inner surface of the distal end portion 44 of the balloon 38 if desired.

The valve member 40 includes a support member 50 shown as an elongate cylindrical plastic member having an airflow passage 51 therethrough, and a duckbill valve 52 connected, for example, by an adhesive or by other suitable means to the left or distal end portion of the valve support member 50. Valve 52 may be molded or formed, for example, of an elastomeric material, such as natural or synthetic rubber or a suitable thermoplastic elastomer. It includes a generally cylindrical portion 54 on member 50, generally triangular opposed sidewalls 55 and 56 (FIGS. 1 and 4) and a pair of opposed distally extending inwardly inclined duck-bill lips 57 and 58 normally resiliently urged into engagement with each other at the distal ends to close the valve. The duck-bill valve 52 is formed as a unitary member with a distal end slit 59 and may be of any conventional or suitable construction in which the lips are maintained closed until a pressure differential in which the interior pressure is greater than the outer pressure, causes the lips to open and allow fluid flow from the proximal interior to the distal exterior of the valve. When such pressure differential ceases, the lips resiliently return to their normally closed position as shown. Any pressure differential in the opposite sense, that is, a positive pressure at the external side, such as within the pressure indicating balloon 38, tends to further urge the lips 58 together to maintain the valve in a closed condition thereby preventing air from flowing from the balloon 38 into the valve and through the valve supporting member 50.

The pump bulb 42 includes a bulbous portion 60 having a vent opening 62 at the proximal end and a cylindrical portion 64 resiliently and frictionally encompassing and secured to the valve support member 50. As shown in the illustrated example, the cylindrical portion 64 of the syringe bulb extends over and surrounds a proximal portion of the cylindrical portion 46 and the support member 50 of the valve member 40 to form a fluid tight fixed connection between the bulb 42 and the valve member. The bulb 42 is resiliently compressible and may be formed of a elastomeric material, such as natural or synthetic rubber or an elastomer plastic, that will allow the bulbous portion to be collapsed by the hand and when the collapsing forces are removed, the bulbous portion 60 will return to its preformed or molded bulbous shape, such as shown in FIGS. 1 and 2.

In use, with the cuff 14 deflated, the endotracheal tube 12 may be inserted into the patient, either by way of the nasal or oral passages, so that the cuff 14 is within the trachea. The cuff inflation control device 16, which is, of course, external to the patient, is then manually operated by hand to inflate the cuff. The inflated cuff closes off the patient's airway or trachea between the outer surface of tube 12 and the walls of the trachea. Then, the proximal end 22 of tube 12 may be connected to a source of gas for supplying a desired gas, such as air, oxygen or anesthesia, to the lungs of the patient.

The cuff 14 is inflated by grasping the syringe bulb 42 in the hand and covering the vent opening 62 with one of the fingers, such as the thumb, and then squeezing the bulb to collapse it thereby causing air that was in the bulb to pass through the passage 51 and open the lips 57 and 58 of the duck-bill valve 52 thereby allowing air to move into the indicator balloon 38 and into the inflation conduit 36. Air flows through the inflation lumen 20 to the interior of the cuff 14 effecting expansion of expansible portion 32 of the cuff. The inflated cuff 14 provides a seal between the tube 12 and the walls of the trachea. Since the inflation balloon 38 is in series flow relationship with the cuff 14, the valve member 40 and the pump bulb 42, the pressure indicating balloon 38 will also expand with the increase in pressure thereby providing an indication of the pressure condition of the cuff within the patient, both visually and by feel. With the cuff 14 and the indicating balloon expanded, the duckbill valve 52 will be closed and prevent reverse air flow into the valve and support member passage 51.

During inflation of cuff 14, the resilient bulb 42 may be collapsed with the vent 62 closed by the thumb and then, of course, the thumb may be moved away from vent opening 62 to allow further air to enter the bulb so that the bulb will expand when not being collapsed by the hand. This may be repeated a sufficient number of times to expand the cuff 14 in a desired manner.

When it is desired to reduce the pressure inside the cuff 14 to the opposed sides of the duck-bill valve are pinched or urged toward each other to bend the distal ends of the lips 59 and 58 apart to thereby open the slit 59 (FIG. 5) and the valve 52 as illustrated in FIG. 6. The valve 52 may be pinched by simultaneously pinching opposed sides of the balloon 38 and distal ends of the sidewalls 55 and 56 of the valve such as with the index finger and thumb as shown. When the valve 52 is opened, air from the cuff 14 can flow into the inflation lumen 20, tube 36, balloon 38, through hllow duck-bill valve 52, passage 51, into bulb 42 and through vent 62 to the atmosphere thereby reducing the pressure within the cuff. If the valve 52 is maintained in the open condition as in FIG. 6 for a sufficient length of time, the cuff 14 will deflate and return to its original shape as seen in FIG. 1 due to the resiliency of the elastomeric material of the cuff. The indicating balloon 38 will also be collapsed or partially collapsed since the balloon is in fluid communication with the cuff. The endotracheal tube 10 may be removed from the patient while the cuff is deflated.

When desired, the valve 52 can be manually only slightly opened or it can be repeatedly opened and closed to easily adjust the pressure within the cuff 14 and indicating balloon 38. Thus, the cuff inflation control device 16 can be manually readily operated to control the cuff inflation over a range of pressures from a relatively high pressure to a low pressure within the cuff. The control is easily performed by suitably pinching the opposed sides of the balloon 38 at the duck-bill valve 52 to pinch and open the valve. Removing the pinching forces, of course, allows the valve 52 to close. The pump bulb 42 is continuously connected to the valve and indicating balloon and is always available for pumping air into the cuff 14. Also, the bulb 42 and vent 62 in the proximal end of the bulb provide the airflow path for venting air to the atmosphere during a reduction of air pressure in the cuff 14. Thus, the vent 62 provides both inlet and outlet air flow for the inflation control unit 16.

When the cuff 14 is deflated, the indicating balloon 38, when of the type which is preformed in a bulbous shape, is generally irregular in the collapsed condition such as illustrated in FIGS. 1 and 4. Where the indicating balloon 38 is of the "tight-to-shaft" type, the elasticity of the balloon will cause it to return to its preformed shape which may be generally cylindrical. In either case, the balloon will provide a readily visible indication of whether the cuff is inflated or not.

With the duck-bill valve 52 disposed within the indicating balloon 38, the device is especially compact and relatively small in overall size, and the duck-bill valve is easily manipulated within the indicating balloon. Also with the pump bulb 42 connected directly to the valve 40, the size of the control device is further reduced. While the duck-bill valve 52 is disposed within the bulbous portion 43 of the indicating balloon so as to minimize the overall size of the control device 16 and to provide easy manual control of the valve by pinching the valve through the balloon, various other constructions are possible. For example, the duck-bill valve 52 may be disposed within the cylindrical portion 46 of the balloon with the cylindrical portion 46 either integrally connected or connected by bonding or cement or the like to the balloon or valve.

As various changes could be made in the above construction without departing from the scope of the invention, it is intended that all matter contained the above description and apparatus shown in the accompanying drawing shall be interpreted as illustrative and not in a limiting sense.

What is claimed is:

1. A medical tube device comprising a tube having a portion thereof for insertion into a body cavity, an inflatable cuff connected to said tube portion, passage means connected at one end with said cuff for conveying inflating fluid to inflate said cuff when in the body cavity, a pressure indicating balloon connected at the opposite end of said passage means in fluid communication with said cuff for providing an indication of the fluid pressure condition of said cuff, hand operated fluid pressure pump means connected in fluid communication with said balloon for inflating said balloon and said cuff with fluid, and one-way valve means indicating a pair of opposed resilient valve members normally in engagement with each other to close said valve means and being connected within said balloon to allow fluid to flow in a direction therethrough from said pump means to said balloon in response to the pressurization of fluid in said pump means for inflating said cuff and normally preventing fluid flow therethrough in the opposite direction, said valve members and a portion of said balloon being manually simultaneously squeezable to open said valves means and allow fluid flow through said valve means in the opposite direction for reducing fluid pressure in said cuff.

2. The device of claim 1 wherein said valve members respectively include duck-bill lips disposed within said balloon and squeezable to open said valve means.

3. The device of claim 1 wherein said balloon includes an expansible portion and a sleeve portion connected to said valve means.

4. The device of claim 3 wherein said valve means includes a relatively rigid support member having a passage therethrough, and said balloon and pump means are connected to said support member so that fluid flow between said pump means and said balloon flows through said passage.

5. The device of claim 4 wherein said valve means extends into said expansible portion of said balloon.

6. The device of claim 5 wherein said valve reduction of pressure in resilient, normally cosed elastomeric duck-bill lips extending into said expansible portion of said balloon.

7. The device of claim 6 wherein said duck-bill lips and said expansible portion of said balloon are simultaneously squeezable to open said duck bill lips.

8. The device of claim 7 wherein said cuff comprises a sleeve of an elastomeric material which lies closely adjacent said tube when uninflated.

9. The device of claim 1 wherein said pump means includes a hollow resiliently compressible hand squeezable bulb.

10. The device of claim 9 wherein said bulb has a vent opening to the atmosphere which is adapted to be manually closed when air is to be forced into said cuff to inflate the same.

11. The device of claim 1 wherein said cuff comprises an elastomeric sleeve closely adjacent the outer surface of said tube throughouts its length when uninflated.

12. The device of claim 11 wherein said passage means includes a flexible inflation conduit extending from said tube and connected to said balloon and supporting said balloon, valve means and bulb from said tube.

13. A medical tube device comprising a flexible plastic tube having a portion adapted for insertion into a body cavity, an air inflatable cuff surrounding said tube portion and having opposed ends sealingly connected to said portion, passage means connected at one end with the interior of said cuff and including a conduit extending from said tube, and means for controlling the inflation and deflation of said cuff including an inflatable pressure indicating balloon connected at one end to said conduit for fluid communication with the interior of said cuff, a hand-squeezable resilient air pressure bulb for supplying pressurized air to said balloon and said cuff, and a one-way duck-bill valve having normally closed resilient duck-bill lips disposed within said balloon and connected in series fluid flow relation between said balloon and said bulb to allow air to flow from said bulb to said balloon when air is pressurized in said bulb and during inflation of said cuff and to normally prevent air flow from said balloon to said bulb when the pressure in said balloon exceeds that in said bulb, a portion of said balloon and said duck-bill lips being manually simultaneously squeezable to open said duck-bill lips and allow air to flow through said valve means from said balloon to said bulb for reducing air pressure in said cuff.

14. The device of claim 13 wherein said valve means includes a support member connected to said duck-bill valve and having a passage therethrough in series flow relation with said balloon and said bulb, the other end of said balloon and one end of said bulb being connected to support member.

15. The device of claim 14 wherein portions of said balloon, duck-bill value and said bulb all surround said support member.

16. The device of claim 13 wherein said cuff is of an elastomeric material and generally cylindrical with its inner surface closely adjacent the outer surface of said tube substantially throughout the length of said cuff when deflated.

17. The device of claim 13 wherein said pressure bulb includes vent opening means adapted to be manually closed when said pressure bulb is squeezed to increase pressure in said cuff, said vent opening means venting air from said bulb to the atmosphere during deflation of said cuff.

18. The device of claim 17 wherein said vent opening means is the only vent to the atmosphere in said means for controlling the inflation and members respectively include said cuff whereby all air into and out of the same flows through said vent opening means.

19. A medical tube device comprising a flexible plastic tube having a portion adapted for insertion into a body cavity, an air inflatable cuff surrounding said tube portion and having opposed ends sealingly connected to said portion, passage means connected at one end with the interior of said cuff and including a conduit extending from said tube, and means for controlling the inflation and deflation of said cuff including an inflatable pressure indicating balloon connected at one end to said conduit for fluid communication with the interior of said cuff, a hand-squeezable resilient pressure bulb for supplying pressurized air to said balloon and said cuff, and a one-way valve extending within said balloon and connected in series fluid flow relation between said balloon and said bulb to allow air to flow from said bulb to said balloon when air is pressurized in said bulb and during inflation of said cuff and to normally prevent air flow from said balloon to said bulb when the pressure in said balloon exceeds that in said bulb, said one-way valve being manually squeezable by simultaneously squeezing a portion of said balloon and said one-way valve to open said one-way valve and allow air to flow from said balloon to said bulb for for reducing air pressure in said cuff.

* * * * *